US012797025B2

(12) United States Patent
Luke et al.

(10) Patent No.: US 12,797,025 B2
(45) Date of Patent: Nov. 17, 2026

(54) MANDIBULAR CANAL DETECTION

(71) Applicant: Ajman University, AJman (AE)

(72) Inventors: Alexander Maniangat Luke, Ajman (AE); Khaled Assaleh, Ajman (AE); Kamran Arshad, Ajman (AE); Sam Thomas Kuriadom, Ajman (AE); Qammer H Abbasi, Ajman (AE); Muhammad Imran, Ajman (AE); Adnan Qayyum, Ajman (AE); Muhammad Zakir Khan, Ajman (AE)

(73) Assignee: Ajman University, Ajman (AE)

( * ) Notice: Subject to any disclaimer, the term of this patent is extended or adjusted under 35 U.S.C. 154(b) by 119 days.

(21) Appl. No.: 18/957,722

(22) Filed: Nov. 23, 2024

(65) Prior Publication Data

US 2026/0144512 A1 May 28, 2026

(51) Int. Cl.

*A61B 6/51* (2024.01)
*A61B 6/00* (2006.01)
*A61B 6/03* (2006.01)

(52) U.S. Cl.

CPC .................................... *A61B 6/51* (2024.01); *A61B 6/03* (2013.01); *A61B 6/5223* (2013.01)

(58) Field of Classification Search

CPC ........................................................ A61B 6/51
See application file for complete search history.

(56) References Cited

U.S. PATENT DOCUMENTS

| | | | | |
|---|---|---|---|---|
| 6,954,730 | B2 * | 10/2005 | Lau | G16H 20/40 706/924 |
| 10,460,839 | B1 * | 10/2019 | Ricci | G16H 50/20 |
| 2002/0188478 | A1 * | 12/2002 | Breeland | G16H 10/60 705/3 |
| 2011/0026671 | A1 * | 2/2011 | Shi | A61B 6/51 378/39 |
| 2014/0009573 | A1 * | 1/2014 | Fujita | A61B 6/5241 348/36 |
| 2016/0128624 | A1 * | 5/2016 | Matt | A61B 5/4542 600/301 |
| 2016/0249850 | A1 * | 9/2016 | Afifi | A61C 9/004 600/407 |
| 2017/0014169 | A1 * | 1/2017 | Dean | A61B 17/8071 |
| 2017/0018084 | A1 * | 1/2017 | Mah | G06T 7/0016 |
| 2022/0068039 | A1 * | 3/2022 | Roberts | A61B 6/463 |
| 2024/0029901 | A1 * | 1/2024 | Ezhov | G16H 10/60 |
| 2024/0144598 | A1 * | 5/2024 | Ripoche | G06T 17/20 |
| 2025/0312128 | A1 * | 10/2025 | Yong | A61B 6/582 |
| 2025/0356496 | A1 * | 11/2025 | Shin | A61B 6/5229 |

* cited by examiner

*Primary Examiner* — Hugh Maupin

(57) ABSTRACT

A method includes receiving two-dimensional images. The two-dimensional images are slices from three-dimensional electronic scans. The two-dimensional images are for a region of interest within a person's mouth. The method includes generating a benchmark database. The benchmark database includes views of different mouth areas, previous information from dentists relating to annotations on the views of the different mouth areas, bilateral mandible electronic images; and unilateral mandible electronic images. The method includes determining a mandibular canal area with the person's mouth.

5 Claims, 26 Drawing Sheets

300

400

500

(a) ROI (mandible, i.e., lower jaw) Extraction

| Backbone | #Images | Attention U-Net | | | Standard U-Net | | |
|---|---|---|---|---|---|---|---|
| | | Accuracy | mIoU | Dice | Accuracy | mIoU | Dice |
| ResNet34 | 33 | 0.9903 | 0.6323 | 0.7747 | 0.9904 | 0.6381 | 0.7791 |
| ResNet50 | | **0.9912** | **0.6661** | **0.7996** | 0.9907 | 0.6472 | 0.7858 |
| ResNet101 | | 0.9902 | 0.6315 | 0.7742 | 0.9902 | 0.63 | 0.773 |
| VGG11 | | 0.9797 | 0.3733 | 0.5437 | 0.98 | 0.3664 | 0.5363 |
| VGG16 | | 0.9795 | 0.3488 | 0.5172 | 0.9788 | 0.3354 | 0.5023 |
| VGG19 | | 0.9783 | 0.3051 | 0.4675 | 0.9797 | 0.3382 | 0.5055 |

FIG. 12

(a) Training Loss (b) Validation Loss

TABLE 1600

| Model | Backbone | #Images | Accuracy | mIoU |
|---|---|---|---|---|
| FCN | ResNet50 | 33 | 0.9806 | 0.6212 |
| | ResNet101 | | 0.9758 | 0.4879 |
| DeepLabv3 | ResNet50 | | 0.9764 | 0.4883 |
| | ResNet101 | | 0.9758 | 0.4879 |
| | MobileNetv3 | | 0.9829 | 0.6989 |

FIG. 16

TABLE 2100

| Backbone | #Images | Attention U-Net | | | Standard U-Net | | |
|---|---|---|---|---|---|---|---|
| | | Accuracy | mIoU | Dice | Accuracy | mIoU | Dice |
| ResNet34 | 7 | 0.9879 | 0.5738 | 0.7292 | 0.9877 | 0.5692 | 0.7255 |
| ResNet50 | | **0.9892** | **0.6301** | **0.7731** | 0.9893 | 0.6068 | 0.7553 |
| ResNet101 | | 0.9886 | 0.5848 | 0.738 | 0.988 | 0.5767 | 0.7315 |
| VGG11 | | 0.9742 | 0.2338 | 0.379 | 0.9745 | 0.2588 | 0.4112 |
| VGG16 | | 0.9731 | 0.223 | 0.3646 | 0.9748 | 0.1741 | 0.2966 |
| VGG19 | | 0.9721 | 0.1512 | 0.2627 | 0.9772 | 0.1931 | 0.3237 |

FIG. 21

MANDIBULAR CANAL DETECTION

BACKGROUND

Detection of the mandibular canal (also referred to as the Inferior Alveolar Nerve (IAN) canal) in dental images is an important task conducted in the preoperative planning of dental surgeries. In traditional dental practice, this is often done manually by dental radiologists to avoid damage to the IAN inside the mandibular canal. Various studies have proposed the use of Machine Learning (ML) and Deep Learning (DL) techniques for the automatic detection of mandibular canals. However, the practicality of these methods is hindered by various challenges like the availability of representative datasets comprising good quality images and annotations. Accordingly, there is currently no effective method to scan this particular area of the mouth using such techniques.

BRIEF DESCRIPTION OF DRAWINGS

FIG. 12 is a diagram of an example table;

FIG. 16 is a diagram of an example table;

FIG. 21 is a diagram of an example table;

DETAILED DESCRIPTION OF PREFERRED EMBODIMENTS

The following detailed description refers to the accompanying drawings. The same reference numbers in different drawings may identify the same or similar elements.

Systems, devices, and/or methods described herein are to determine the location of the mandibular canal (also referred to as the Inferior Alveolar Nerve (IAN) canal) within a person's mouth by using two-dimensional (2D) panoramic slices extracted from three-dimensional (3D) CBCT) Cone Beam Computed Tomography) scans (also known as the Mandibular Canal Detection Dataset (MCD2).

In embodiments, a benchmark database for mandibular canal segmentation named Mandibular Canal Detection Dataset (MCD2) is generated. In embodiments, the MCD2 database contains a number of unilateral mandible slices that have been extracted from panoramic slices generated using 3D CBCT dental scans that have different views, i.e., full, medium, and small views. In embodiments, the MCD2 database provides bilateral (full view panoramic) mandible slices. Furthermore, to benchmark MCD2, different state-of-the-art neural network architectures are used and include (but not limited to) standard U-Net, Attention U-Net, DeepLabv3, and Fully Convolution Network (FCN). In addition, different backbone networks across different families of classification models with these models, namely ResNets, mobilenet, and VGG are used.

Figure 1:
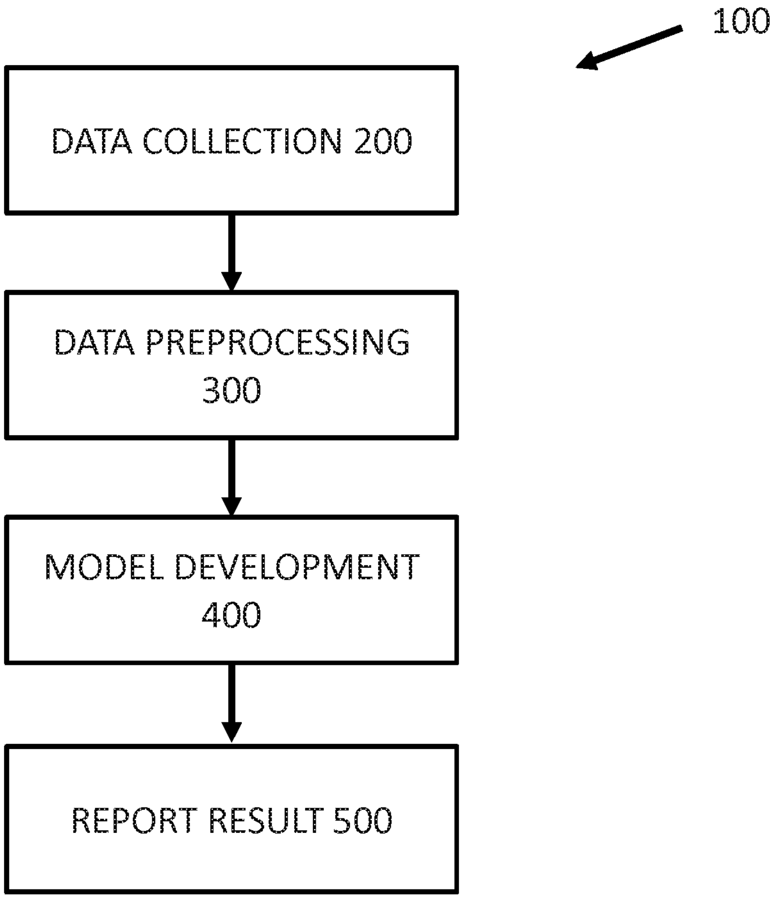
FIG. 1 is a diagram of example flow diagram.
Figure 2:
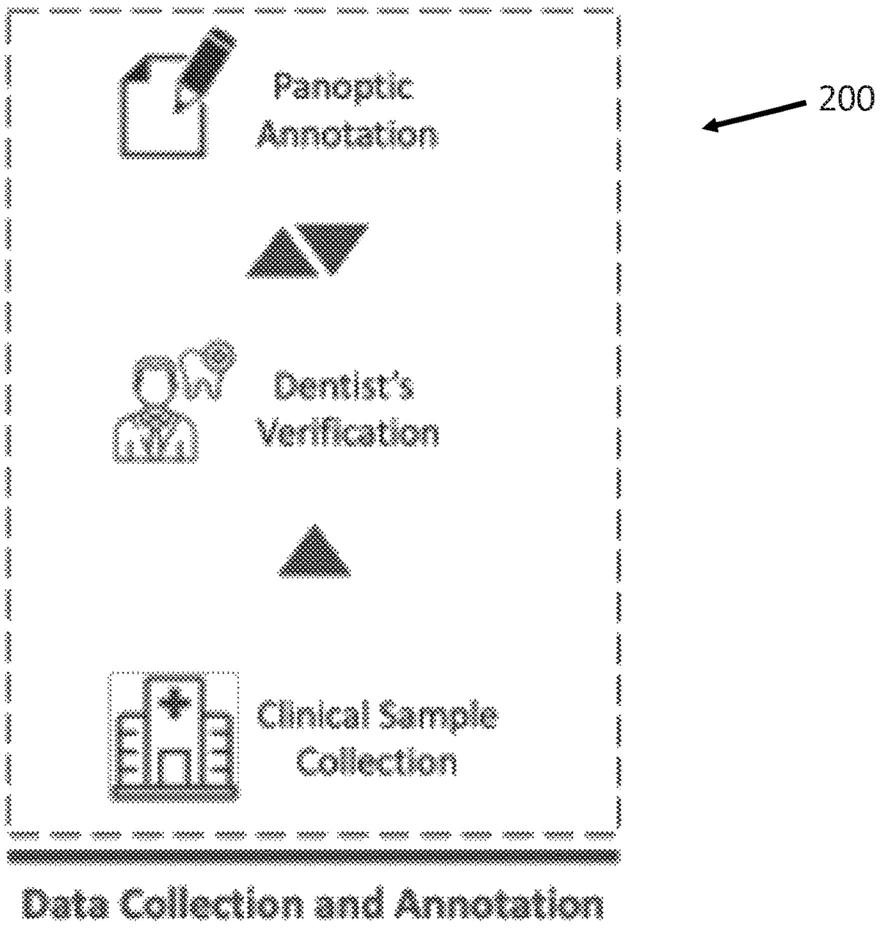
FIGS. 2, 3, 4, and 5 are diagrams of example modules.

FIG. 1 describes a flowchart process 100 for obtaining electronic information and using that electronic information to determine the location of the IAN canal. As shown in FIG. 1, process 100 includes modules 200, 300, 400, and 500. In embodiments, data collection 200 includes sample collection from the clinical environment and panoptic annotation. In embodiments, the 3D CBCT images can be collected using the CS 9300 3D scanner that produces images having dimensions of 150 μm×150 μm×150 μm voxels. In embodiments, the density of the collected images may vary 49.9 μmm to 150 μmm and for better representation of the mandibular canal, the slices are sampled at the density of 1.1 μmm. FIG. 2 further describes module 200.

Figure 3:
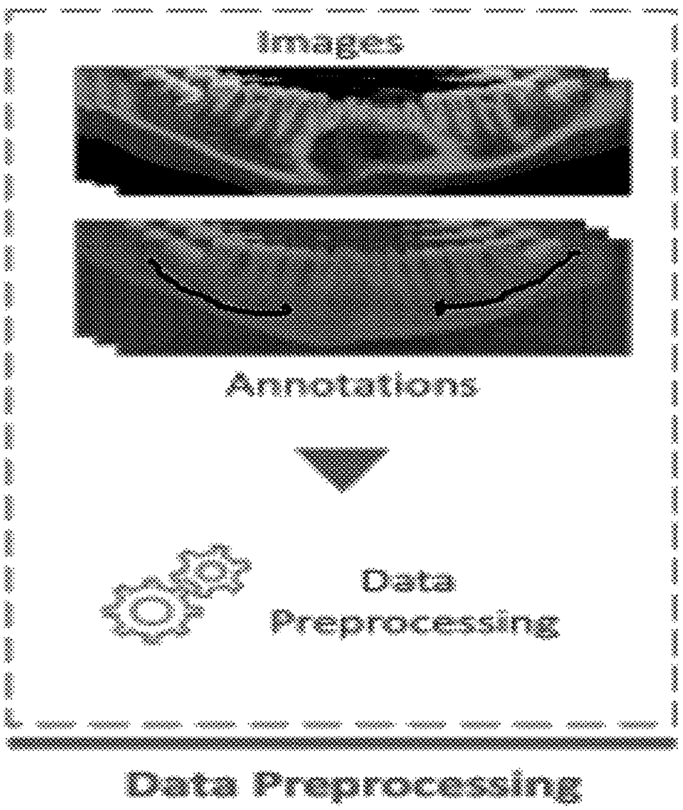
Figure 6:
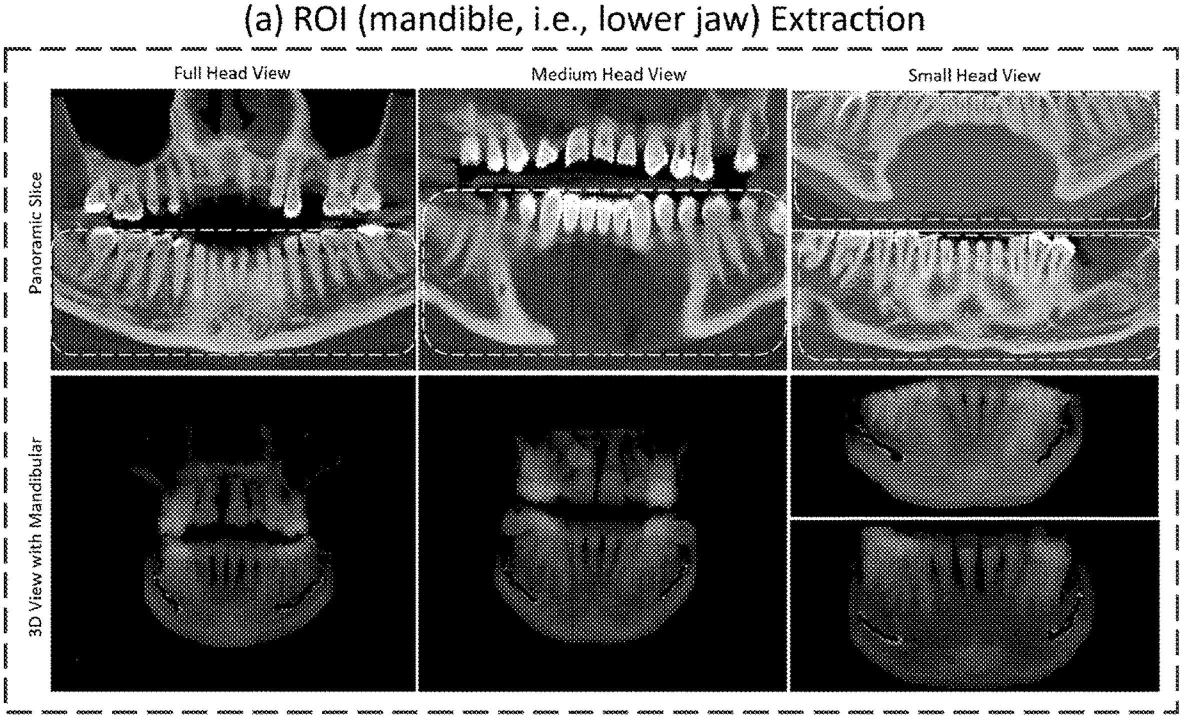
FIG. 6 is a diagram of an example image.

In embodiments, the 3D CBCT scans are obtained from individuals requiring dental implants in the mandible region. FIG. 3 further describes module 300 which includes a number of preprocessing steps that are applied to the data before data annotation and after data annotation. In embodiments, the collected images have different views, i.e., full head view, medium view, and small view (such as shown in FIG. 6). In embodiments, the region of interest (ROI) of the lower jaw area is extracted before performing data annotation. In embodiments, the extraction of ROI in 3D CBCT scans also avoids extra computations are be wasted in processing irrelevant pixels, which could potentially influence the learning capabilities of ML/DL models. Therefore, eliminating the irrelevant information from training data can save computations and can influence the model to learn relevant features at the same time. In addition, appropriate preprocessing is applied to remove any privacy-related information from the collected dataset.

Figure 4:
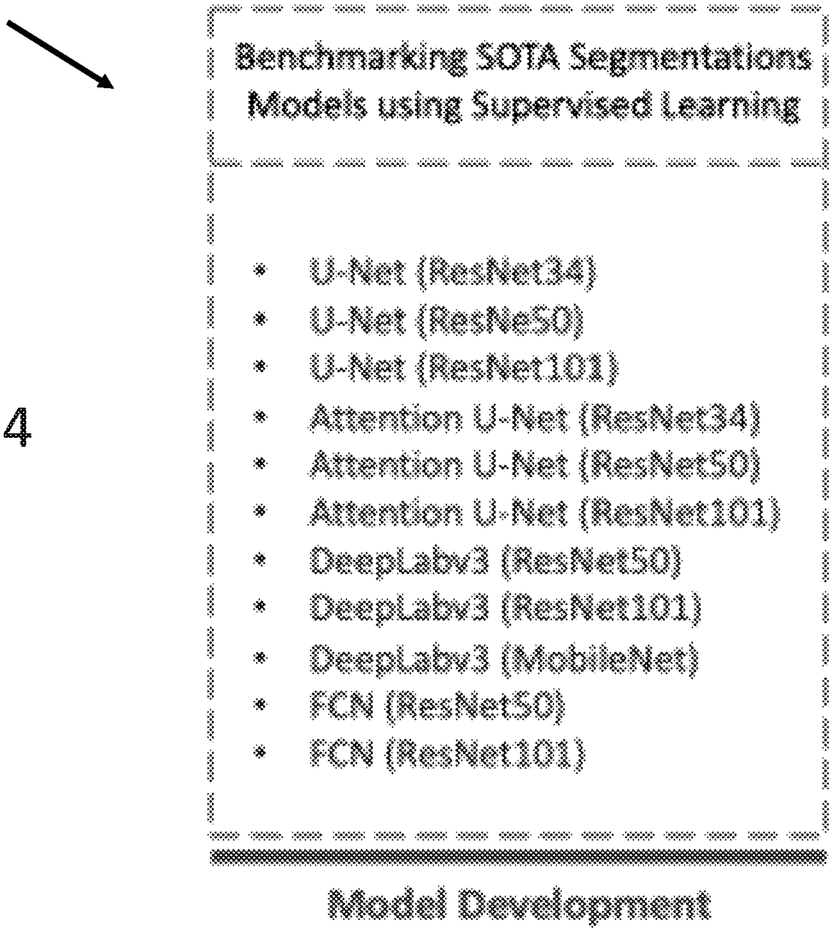
Figure 5:
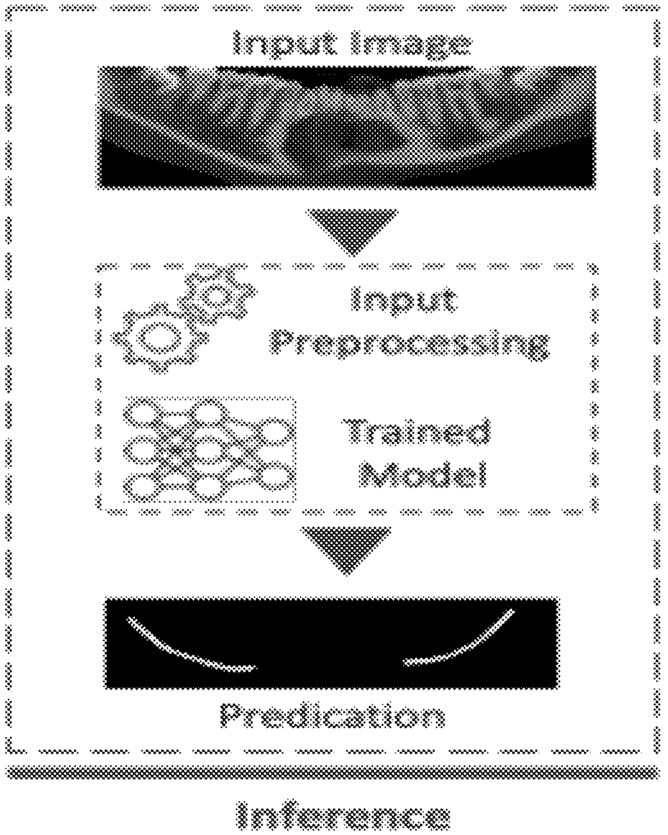

In embodiments, for efficient training of models, precise and pixel-level annotations for the identification of the mandibular canal are required. In embodiments, the data labelling strategy includes: (1) performing the annotation of collected data; (2) defining the annotation guidelines; and (3) validating and rectifying the annotations. In a non-limiting example, a set of 35 images having different quality and varied levels of difficulty in accurately detecting the path of the mandibular canal are annotated by two expert oral radiologists each having more than 20 years of experience. Then the experts trained a team of two technicians to annotate the rest of the images, which are then verified and rectified by the expert oral radiologist to ensure the efficacy of the annotations. As shown in FIG. 4, to benchmark MCD2, different state-of-the-art neural network architectures are used and include (but not limited to) standard U-Net, Attention U-Net, DeepLabv3, and Fully Convolution Network (FCN). In addition, different backbone networks across different families of classification models with these models, namely ResNets, mobilenet, and VGG are used. As shown in FIG. 5, module 500 is further shown in the end results provided in an electronically displayable report.

In embodiments, for annotation of collected 3D CBCT scans and for extracting 2D slices, CareStream (CS) 3D Imaging Software may be used, which is widely used software in dental clinical practice. This software is primarily used for analyzing 3D CBCT images and for preoperative planning of dental implants.

Figure 7:
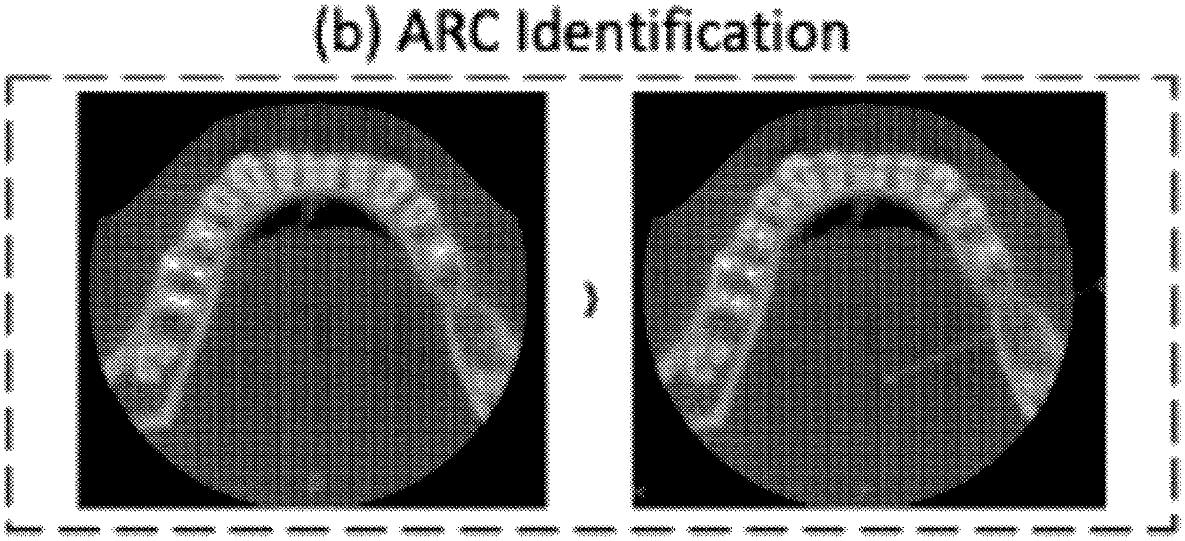
FIG. 7 is a diagram of an example image.
Figure 8:
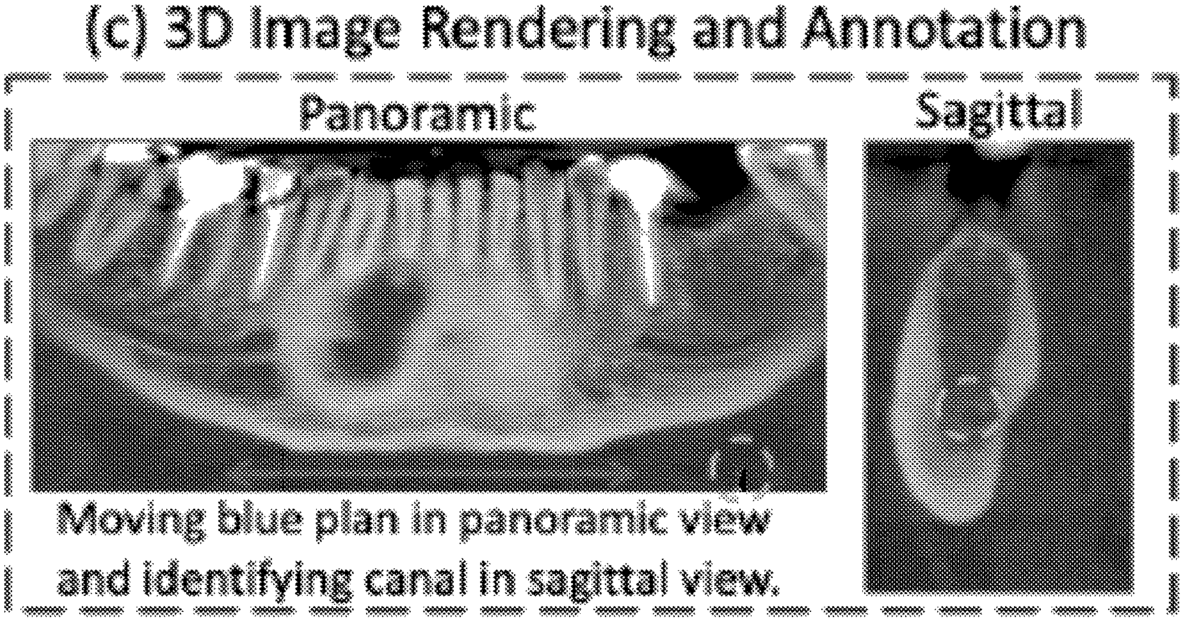
FIG. 8 is a diagram of an example image.

In embodiments, the methodology used for the annotation of CBCT images for the task of mandibular canal detection using CS Imaging Software is further described in FIGS. 6, 7, and 8. As shown FIG. 6, the first step is to extract ROI from the collected 3D CBCT scans. As shown in FIG. 7 ARC identification is performed by generating axial slices from the 3D CBCT scan, which are then used for the generation of respective panoramic and sagittal slices. As shown in FIG. 8, Finally, the mandibular canal path is identified by utilizing the information contained in panoramic and sagittal slices, which is performed by moving the white cursor in the panoramic slice and then identifying the canal opening in the sagittal slice. For identifying the mandibular canal at the right side, the cursor is moved from extreme right to mid until the canal closing point is seen. Similarly, it is moved from the extreme left to the point where the canal ends for the identification of the left mandibular canal.

In embodiments, the electronic data collected for process 100 is obtained from dental patients. In a non-limiting example, the dataset is collected from 89 patients who are about to undergo a dental implant. In this non-limiting example, the patients have different demographics, sex, and age. Out of 89 patients, 35 are female and 54 are male, which have different ethnicity and the ages. In this non-limiting example, the CBCT scans from 39 patients contain full mandible information, i.e., mandibular canal for both sides (left and right), while the remaining 50 patients have undergone only one-sided CBCT scans (i.e., either left or right). Therefore, in this non-limiting example, there are two sets of images of the dataset: (1) a set of 39 2D images containing bilateral mandible; and (2) an augmented set of images containing the unilateral (i.e., single-sided) mandible images including the one containing left and right mandible from full view images.

Figure 9:
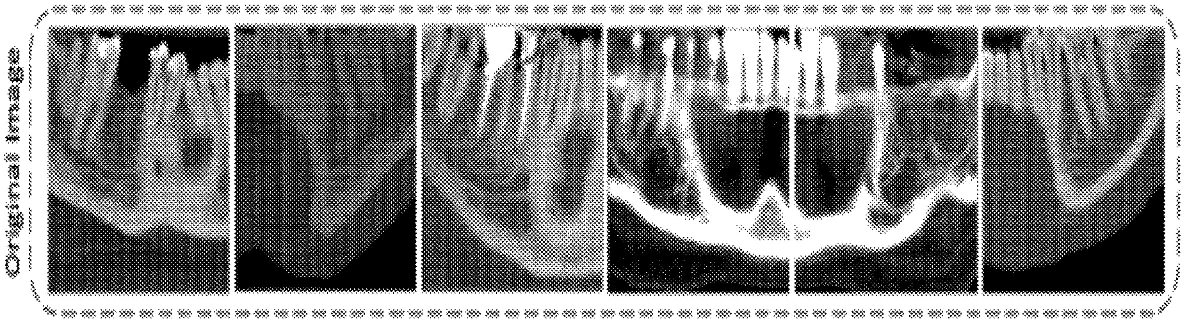
FIGS. 9, 10, and 11 are diagrams of example images.
Figure 10:
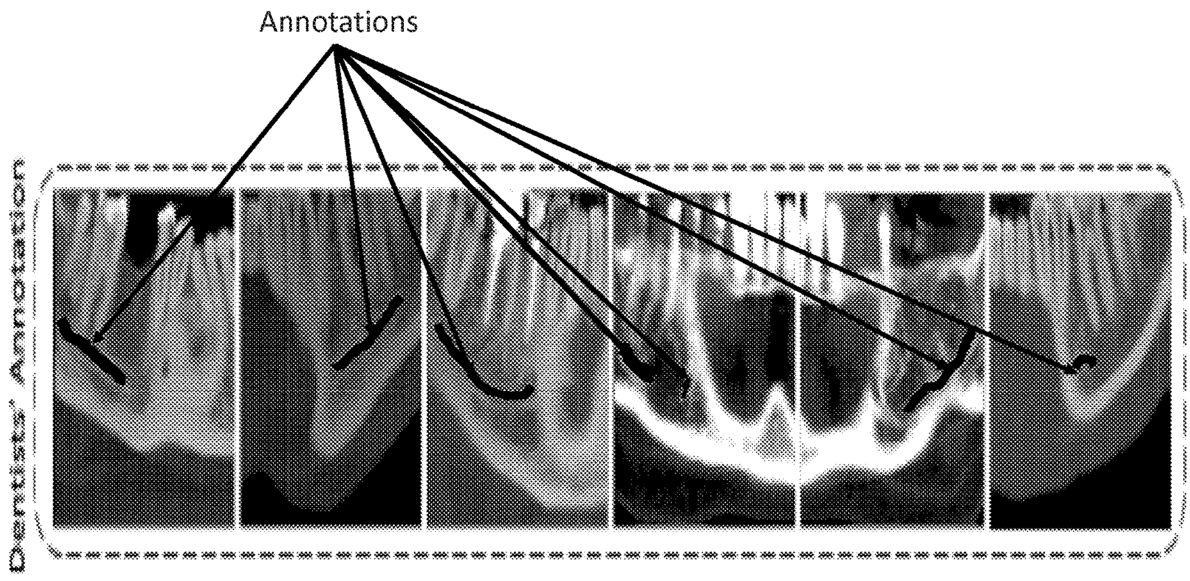
Figure 11:
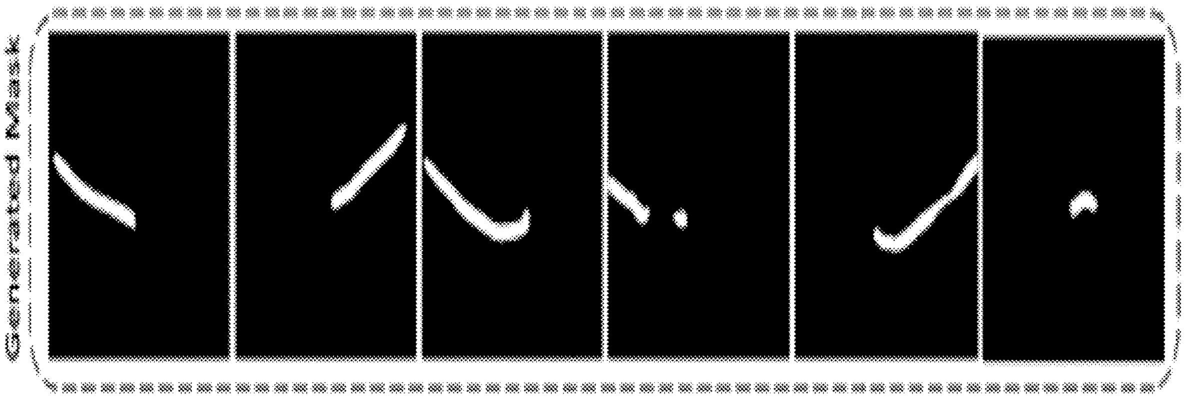

Therefore, in this non-limiting example, the final dataset has a total of 167 images. Visual examples from the collected dataset depicts different variations along with the dentists' annotations and generated masks (for model training) are shown in FIGS. 9, 10, and 11 (respectfully). In embodiments, these figures show that the collected dataset has different variations, i.e., in terms of image quality, annotation location, size, and visibility.

In embodiments, to determine mandibular canal detection, an input CBCT image is split into two distinct (non-overlapping) regions, i.e., foreground (the mandibular canal region) and background (region except mandibular canal information). In embodiments, this formulation includes a typical binary classification task at the pixel level so as to identify which class a particular pixel belongs to. In embodiments, the models are training using the annotated data which is extracted from 3D CBCT scans.

Accordingly, the systems, methods, and/or devices described herein are to learn an unknown function that could map the input image x to the target y such that $f$:x→y. To learn this function f, SOTA (state of the art) segmentation models are trained. In embodiments, the segmentation model is denoted as $M_s$, which is trained using paired training $$D = \{x_i, y_i\}_{i=1}^{N},$$

where $x_i$, and $y_i$ represent the input image and the target (ground-truth) mask, respectively. N is the total number of samples in D, where the input image is denoted as $x_i \in R^{n\times m\times 3}$ and target segmentation mask is defined as $y_i \in \{0,1\}^{n\times m}$, which consists of an image containing pixels intensities of 1 and 0 representing foreground (mandibular canal) and background, respectively. In embodiments, where n and m are the number of rows in input images and masks. The segmentation model $M_s$ is trained using standard loss used for binary classification (as defined in Eq. 1).

$$L(y_k, y'_k) = y_k \log(y'_k - (1 - y_k)\log(1 - y'_k)) \tag{1}$$

Where, $$y'_k$$

denotes the mask predicted by the underlying model and $y_k$ is the reference (ground-truth) mask.

Accordingly, the systems, methods, and/or devices described herein provide for a benchmark dataset for segmenting the mandibular canal. Therefore, segmentation models are evaluated based on an electronic learning process. For example, models are trained and tested on labeled datasets where each input image has a corresponding ground-truth label or annotation. For segmentation tasks, this label is usually a pixel-wise mask, which indicates the class of each pixel (e.g., of the object mandibular canal) and background. In embodiments, the systems, methods, and/or devices described herein are for pixel-level classification where image pixels are classified into the background (non-mandibular canal region) and foreground (mandibular canal region) using binary cross entropy loss (equation 1). In embodiments, the classification is also based on a mask generated by $M_s$ with a reference mask.

For benchmarking of MCD2, four different architectures of deep generative models and six different DL-based backbone architectures are analyzed. This included, but is not limited to, generative models: U-Net (with skip connections) 28, Attention U-Net (with attention mechanism and skip connections) 29, fully convolutional network (FCN) 30, and Deeplab-v331. Furthermore, different architectures of classification models are used across different family of neural networks architectures for vision applications that include: residual network-based architectures (such as, but not limited to, ResNet34, ResNet-50, and ResNet-10132), VGG-based neural networks (such as VGG11, VGG16, and VGG1933), and Mobilenet-v334. In embodiments, these classification models are integrated with the aforementioned generative models to get the benchmark results using MCD2.

In a non-limiting example, the total number of samples collected from the MCD2 dataset may 167. Also, in this non-limiting example, the data is divided into two non-overlapping sets using a split of 80% and 20% for training and testing, respectively. In embodiments, since the ROI size in the collected dataset is different, therefore, all images are resized to a uniform rectangular dimension of 210×300. In embodiments, the models are trained on large-scale datasets for similar segmentation tasks such as semantic segmentation using Microsoft's COCO dataset35. Furthermore, to ensure the efficient training of models, standard data augmentation methods are used for increasing the size of the training set.

For training of standard U-Net and Attention U-Net models (with different backbone models), a batch size of either two (bilateral mandibular images) or four (unilateral mandibular images) may be used. Also, these models are trained for a maximum of 25 epochs using a learning rate (LR) of $1e^{-3}$, where the optimal LR is determined using the LR scheduler, which scales weight adjustments to minimize the network's loss36. In case LR is low, the training advances at a slow pace, which happens due to minor adjustments to model weights. Conversely, a high LR can lead to undesirable divergent behavior. To facilitate model learning, a cyclic LR approach for model training can be used.

Since the purpose of this paper is to benchmark the dataset, therefore, three different widely used performance metrics for the evaluation of the models include: (1) Mean Intersection Over Union (mIoU)—also known as Jaccord similarity index; (2) Dice score—also referred to as F1-score in the evaluation of segmentation models; and (3) average pixel accuracy. Average Pixel Accuracy: The percentage of accurately classified pixels in the model's reconstructed mask is known as average pixel accuracy, mathematically it is defined as:

$$mPA = \frac{1}{N}\sum_{i=1}^{N}\frac{n_{ii}}{c_i}$$

where, mean average pixel accuracy is represented as mPA and N refers to the total number of pixels, $n_{ii}$ denotes the total number of accurately classified pixels as class i, and $c_i$ is the number of pixels predicted as class j. In $n_{ii}$, i.e., actual class labels and predicted class labels are the same (i.e., it denotes true positives). Intersection Over Union (IoU): It is a widely employed in the evaluation of segmentation models, which is also known as the Jaccord similarity index.

In embodiments, IoU calculates the pixel level overlap between the reference and the predicted masks. In embodiments, the IoU measures the overlap between the actual mandibular canal (i.e., human-annotated region) and the mask generated by the model for the potential mandibular canal path. Mathematically, IoU is calculated as:

$$IoU = \frac{TP}{(TP+FP+FN)}$$

where, TP, FP, and TN denote true positive, false positive, and true negative, respectively. Also, IoU is given as:

$$IoU(m, m') = \frac{|m \cap m'|}{|m \cup m'|}$$

where, m and m' represent the reference (ground truth) mask and the predicted mask. Dice Score: It is a commonly utilized similarity metric for the evaluation of segmentation methods. This metric has been widely recognized for evaluating the segmentation quality of medical images. For the binary image segmentation problem (differentiating the background and foreground), the dice score is calculated as:

$$\text{Dice Score} = \frac{2TP}{2TP+FP+FN}$$

To benchmark the collected MCD2 dataset for the mandibular canal segmentation task, evaluated different SOTA models are evaluated. For example, there may be four different models across different families of neural architectures that have been proposed for the modeling of similar segmentation problems. In addition, different architectures of classification models are analyzed when integrated with mainstream segmentation models (also referred to as generative models) and analyzed the effect of neural network architectural choice on the performance of mandibular canal segmentation. Furthermore, baseline experiments can be categorized into two dimensions based on the segmentation models, i.e., using U-Net-based architectures and using other models (for comparative analysis).

For benchmarking of MCD2, standard U-Net and Attention U-Net models as baseline models can be used. In addition, U-Net-based models are widely employed for the benchmarking of medical image segmentation datasets40. The baseline results for standard U-Net and Attention U-Net models when integrated with different backbone classification models are presented in table 1200 shown in FIG. 12. Table 1200 shows that Attention U-Net has provided relatively improved performance for mandibular canal segmentation in terms of different performance measures. Moreover, Attention U-Net with ResNet50 backbone outperform other models. In FIG. 4, learning curves (FIGS. 13 and 14, respectively) are shown for training and validation loss with increasing epochs for demonstrating the effectiveness of MCD2.

Figure 13:
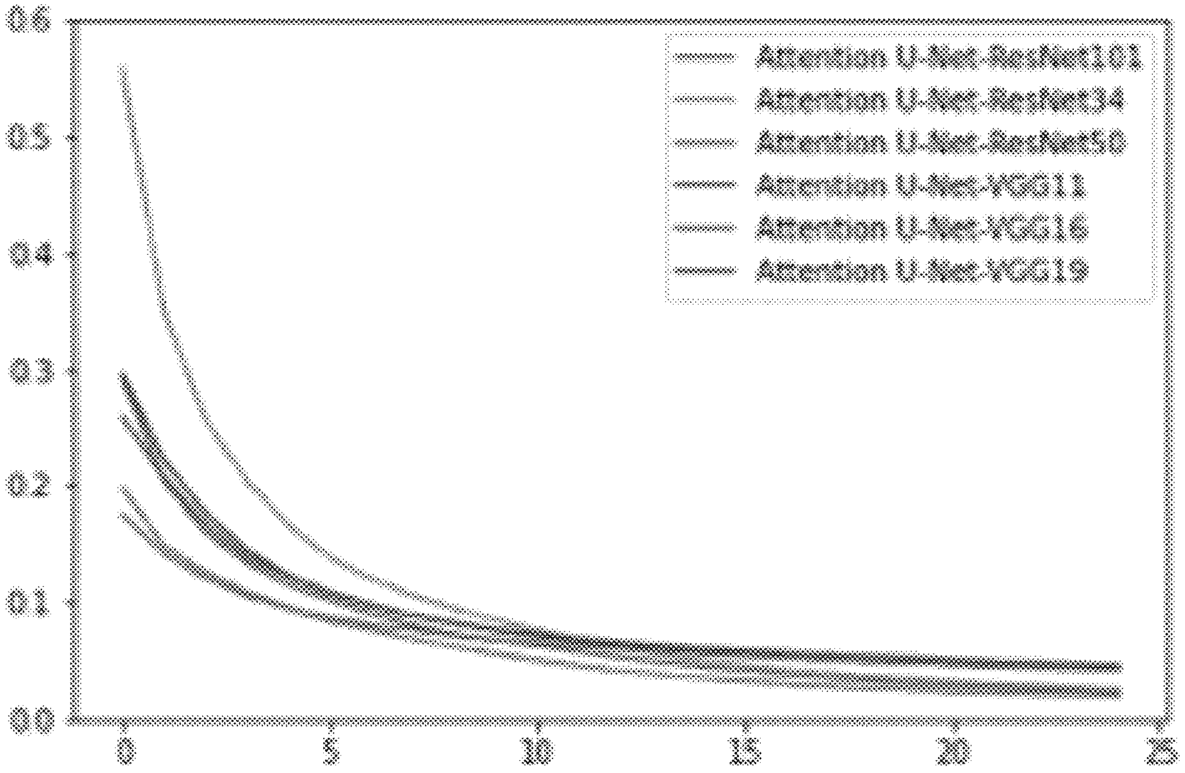
FIGS. 13 and 14 are diagrams of example graphs.
Figure 14:
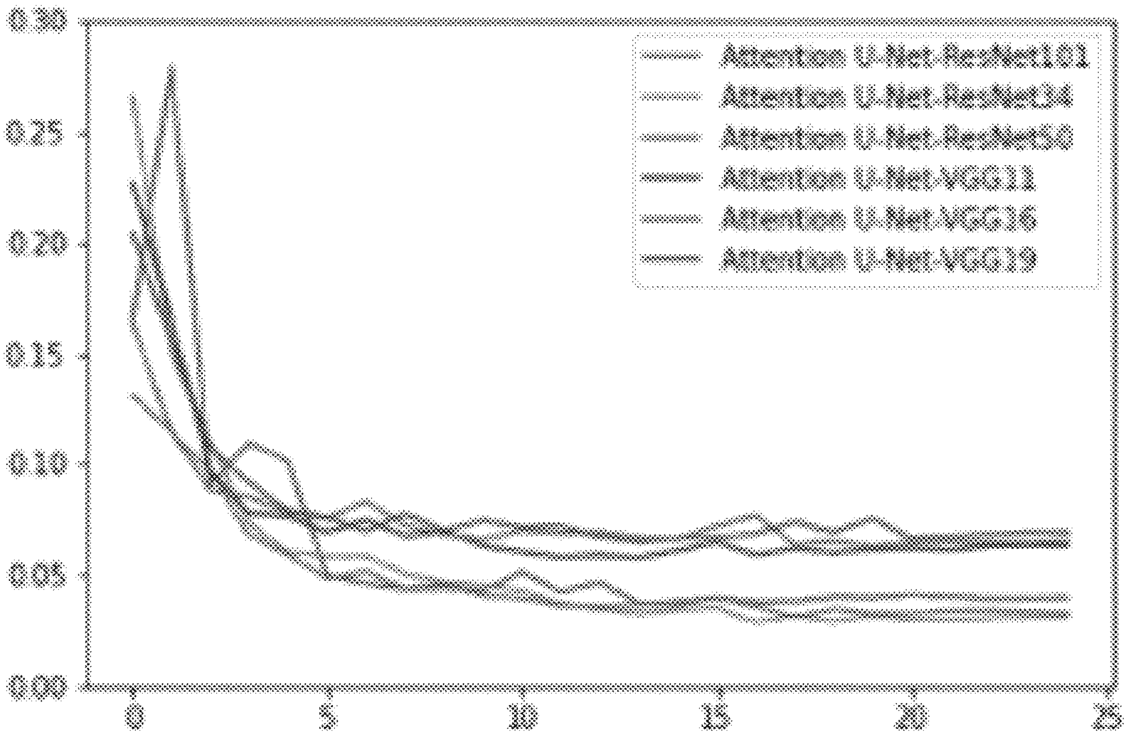
Figures 15A, 15B, 15C, 15D:
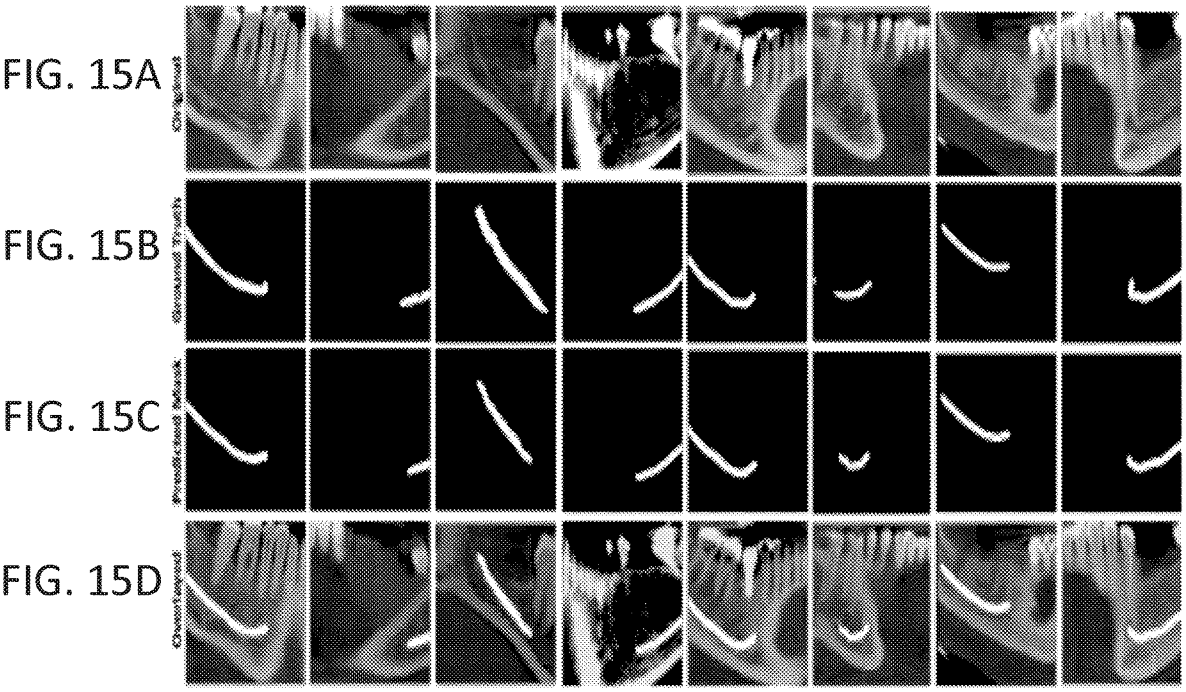
FIGS. 15A, 15B, 15C, and 15D are diagrams of example images.
Figure 17:
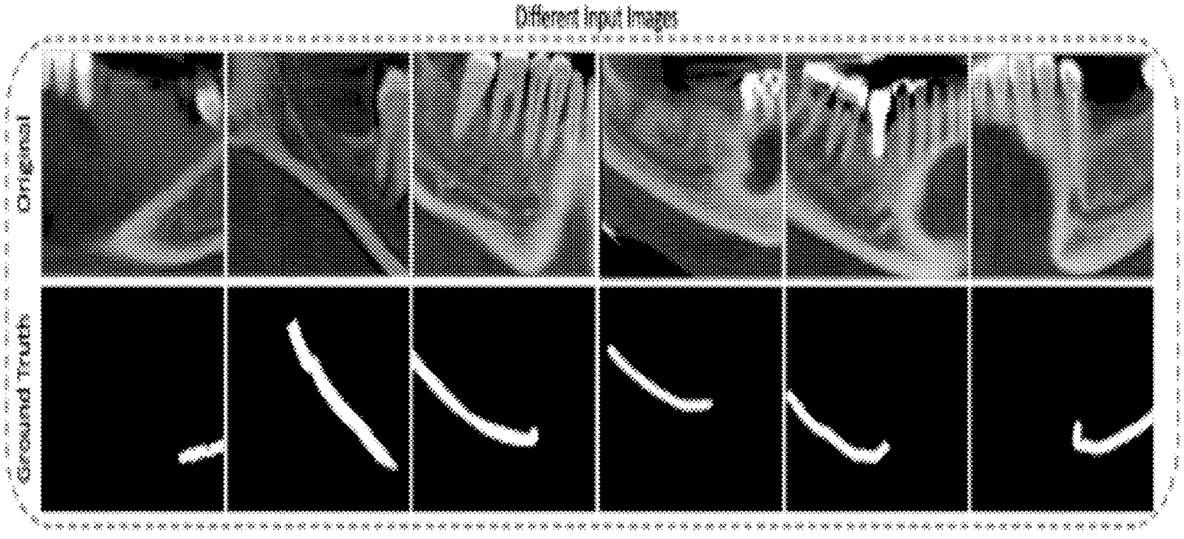
FIGS. 17, 18, 19 and 20 are diagrams of example images.
Figure 18:
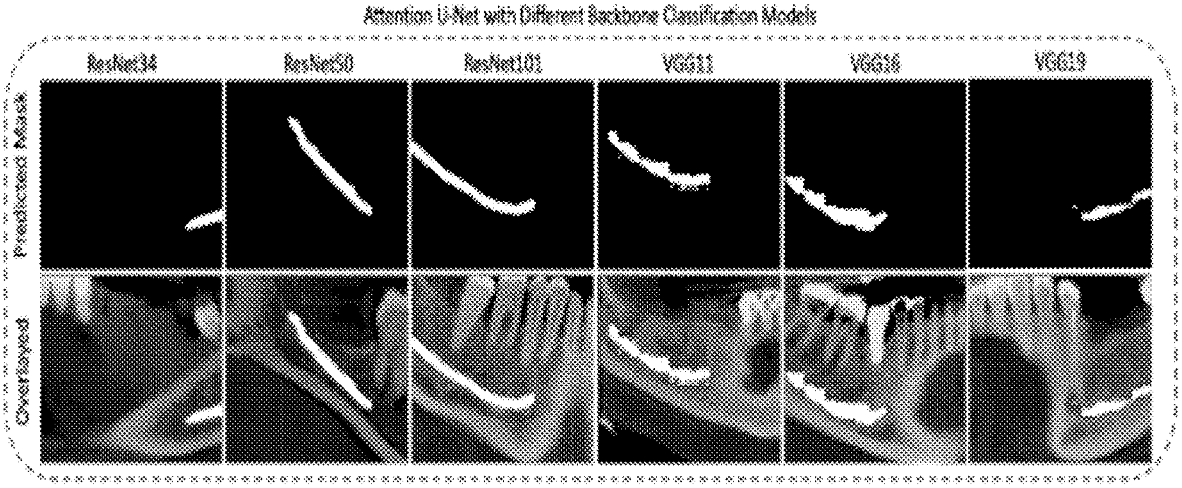
Figure 19:
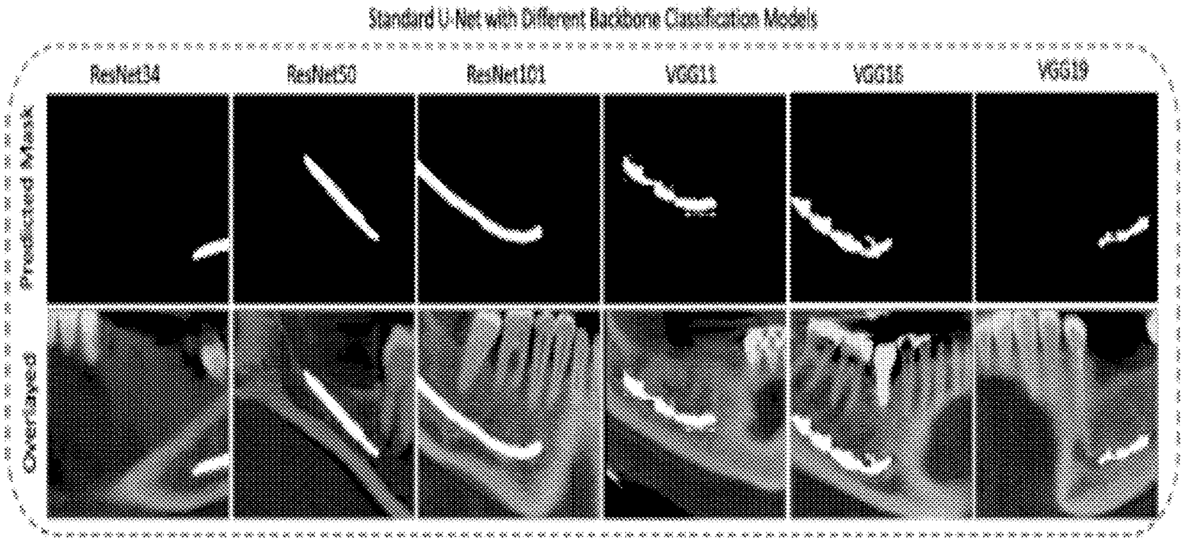
Figure 20:
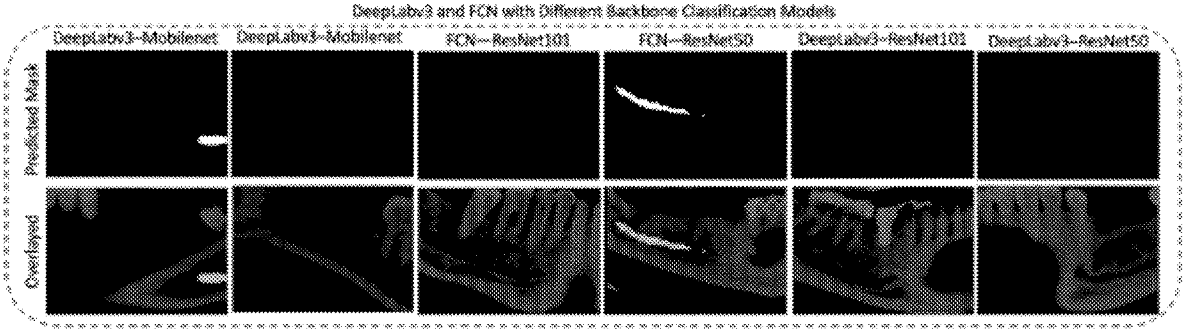
Figures 22A, 22B, 22C, 22D:
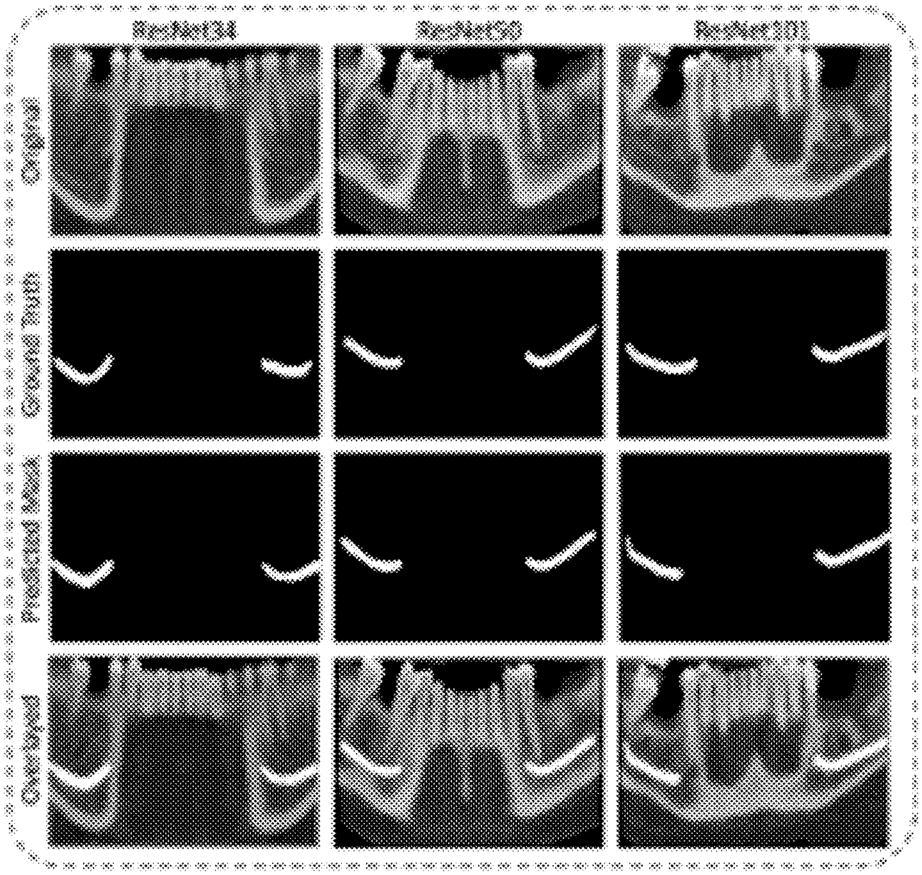
FIGS. 22A, 22B, 22C, and 22D are diagrams of example images.
Figures 23A, 23B, 23C, 23D:
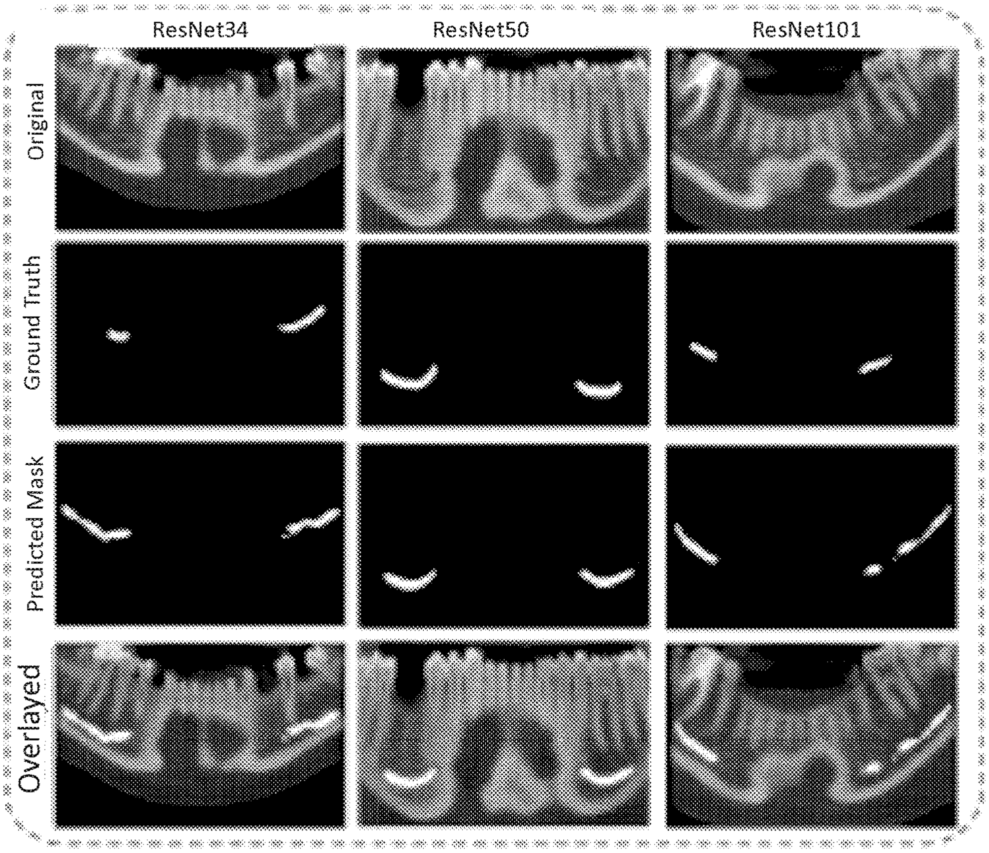
FIGS. 23A, 23B, 23C, and 23D are diagrams of example images.
Figures 24A, 24B, 24C, 24D:
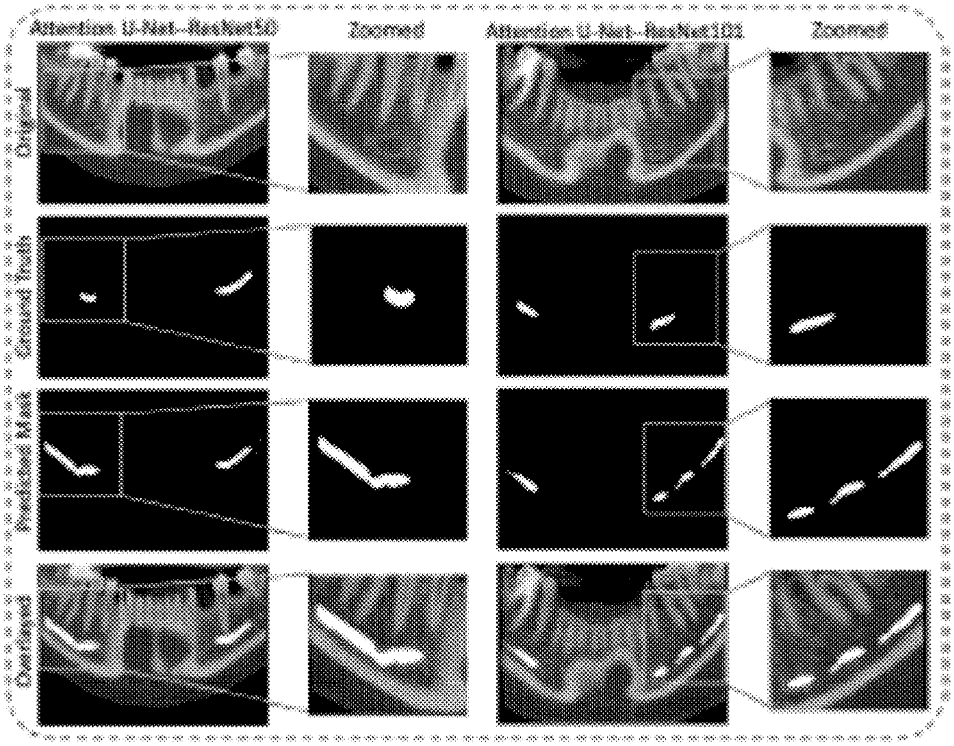
FIGS. 24A, 24B, 24C, and 24D are diagrams of example images.

FIGS. 13 and 14 describe the baseline models smooth learning capabilities using the proposed MCD2. Moreover, FIGS. 13 and 14 show that Attention U-Net-ResNet50 depicted smoother learning as compared to other models. To further highlight the effectiveness of the U-Net with ResNet50 backbone in the detection of the mandibular canal path, visual examples using images depicting different variations in terms of image quality, mandibular canal size, shape, and location (as shown in FIGS. 15A-15D) are used. FIGS. 15A-15D highlight that U-Net having ResNet50 backbone is able to generate such masks that are very close to the human-generated masks.

In addition, to evaluating the performance of U-Net-based models that are considered standard in benchmarking of medical image segmentation approaches. In embodiments, different SOTA models are evaluated that include: DeepLabv3 and FCN while using different backbone models. The results for this analysis are presented in table 1600 in FIG. 16, the performance of these SOTA models is not impressive in terms of different performance metrics.

In embodiments, Table 1600 also shows that DeepLabv3 with MobileNetv3 backbone provided outperformed other models while FCN with ResNet50 backbone performance is second best across all sets of models. In embodiments, these models have very deep architecture and due to this reason, they are more prone to overfitting. On the other hand, Attention U-Net outperformed all other models including standard U-Net, DeepLabv3, and FCN-based neural network architectures, which highlights the effectiveness of incorporating attention mechanism into standard U-Net architecture (compare Table 2 and Table 3). A visual comparison of using different architectures for mandibular canal segmentation can be seen in FIGS. 17 to 20.

FIGS. 17 to 20 demonstrates that on average U-Net-based neural network architectures provided better performance as compared to other models. Also, the performance of using ResNet-based architectures as the backbone network is better as compared to using VGG-based models. ResNet-based models produce such predictions that are very close to human annotations, while VGG-based models introduce visual artifacts (as they mainly produce predictions in square shape. In embodiments, models having mIoU less than 0.5 in Table 3, i.e., DeepLabv3-ResNet50, DeepLabv3-ResNet101, and FCN-ResNet101 failed to produce predictions for the mandibular canal in most cases (see blank predicted masks in FIGS. 17-20).

As described above, MCD2 contains two types of images, i.e., unilateral mandible and bilateral mandible slices. Therefore, bilateral mandibular images (i.e., containing right and left mandible) are used for the task of jointly identifying the mandibular canal on both sides. Based on the performance of Attention U-Net in efficiently identifying the mandibular canal in unilateral slices, the same model architecture is used for this analysis. In addition, for the sake of comparison, the performance of the standard U-Net model is evaluated with different backbone architectures for the reports results for using different backbone classification models with standard U-Net and Attention U-Net in terms of different performance metrics such as mIoU, average pixel accuracy, and average dice score.

As shown in table 2100 (FIG. 21), Attention U-Net with ResNet50 backbone is shown to provide higher performance as compared to other models. A similar observation is noted in the case of using unilateral mandible images. In embodiments, the overall attention-based U-Net architectures provided improved performance as compared to the standard U-Net (with attention) model, which highlights the effectiveness of using Attention U-Net for mandibular canal segmentation. Visual results for using bilateral mandible images are presented in FIGS. 22A-22D, 23A-23D, and 24A-24D which shown detection of mandibular canals in bilateral images.

The results for these experiments are summarized in table 2100, the table reports results for using different backbone classification models with standard U-Net and Attention U-Net in terms of different performance metrics such as mIoU, average pixel accuracy, and average dice score. The table highlights that Attention U-Net with ResNet50 backbone provided higher performance as compared to other models. A similar observation is noted in the case of using unilateral mandible images. Also, the overall attention-based U-Net architectures improved performance as compared to the standard U-Net (with attention) model, which highlights the effectiveness of using Attention U-Net for mandibular canal segmentation. Visual results for using bilateral mandible images are shown in FIGS. 22A-22D, FIGS. 23A-23D, and FIGS. 24A-24D.

In embodiments, the models are trained using bilateral mandible images seem to outperform human annotations in most of the input images while effectively highlighting the potential path of the mandibular canal which is shown in FIGS. 24A-24D. For instance, zoom-in patches can be seen to assess the efficacy of the underlying models in producing candidate predictions for the potential path of the mandibular canal.

Figure 25:
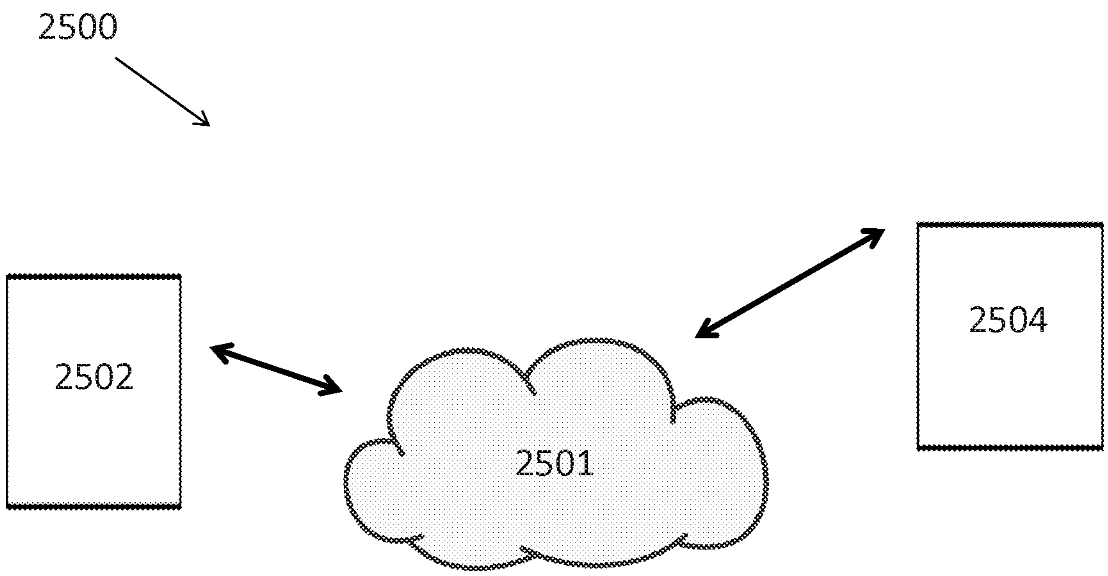
FIG. 25 is a diagram of an example networking environment.

FIG. 25 is a diagram of example environment 2500 in which systems, devices, and/or methods described herein may be implemented. FIG. 25 shows network 2501, device 2502, and analysis system 2504.

Network 2501 may include a local area network (LAN), wide area network (WAN), a metropolitan network (MAN), a telephone network (e.g., the Public Switched Telephone Network (PSTN)), a Wireless Local Area Networking (WLAN), a WiFi, a hotspot, a Light fidelity (LiFi), a Worldwide Interoperability for Microware Access (WiMax), an ad hoc network, an intranet, the Internet, a satellite network, a GPS network, a fiber optic-based network, and/or combination of these or other types of networks. Additionally, or alternatively, network 2501 may include a cellular network, a public land mobile network (PLMN), a second generation (2G) network, a third generation (3G) network, a fourth generation (4G) network, a fifth generation (5G) network, and/or another network.

In embodiments, network 2501 may allow for devices describe any of the described figures to electronically communicate (e.g., using emails, electronic signals, URL links, web links, electronic bits, fiber optic signals, wireless signals, wired signals, etc.) with each other so as to send and receive various types of electronic communications.

Device 2502 may may include any computation or communications device that is capable of communicating with a network (e.g., network 2501). For example, device 2502 may include X-ray machine, a dental imagery machine, a smart phone, a desktop computer, a laptop computer, or another type of computation or communications device.

Device 2502 may receive and/or display content. The content may include objects, data, images, audio, video, text, files, and/or links to files accessible via one or more networks. Content may include a media stream, which may refer to a stream of content that includes video content (e.g., a video stream), audio content (e.g., an audio stream), and/or textual content (e.g., a textual stream). In embodiments, an electronic application may use an electronic graphical user interface to display content and/or information via device 2502. Device 2502 may have a touch screen and/or a keyboard that allows a user to electronically interact with an electronic application. In embodiments, a user may swipe, press, or touch device 2502 in such a manner that one or more electronic actions will be initiated by device 2502 via an electronic application. User device 2502 may receive electronic information from analysis system 2506 and generate and display graphs such as those described in the figures above.

Device 2502 may include a variety of applications, such as, for example, an e-mail application, a telephone application, a camera application, a video application, a multimedia application, a music player application, a visual voice mail application, a contacts application, a data organizer application, a calendar application, an instant messaging application, a texting application, a web browsing application, a blogging application, and/or other types of applications (e.g., a word processing application, a spreadsheet application, etc.). In embodiments, user device 2502 may be used to generate graphs (such as those described in FIGS. 13 and 14) to model various features determined by analysis system 2506.

Figure 26:
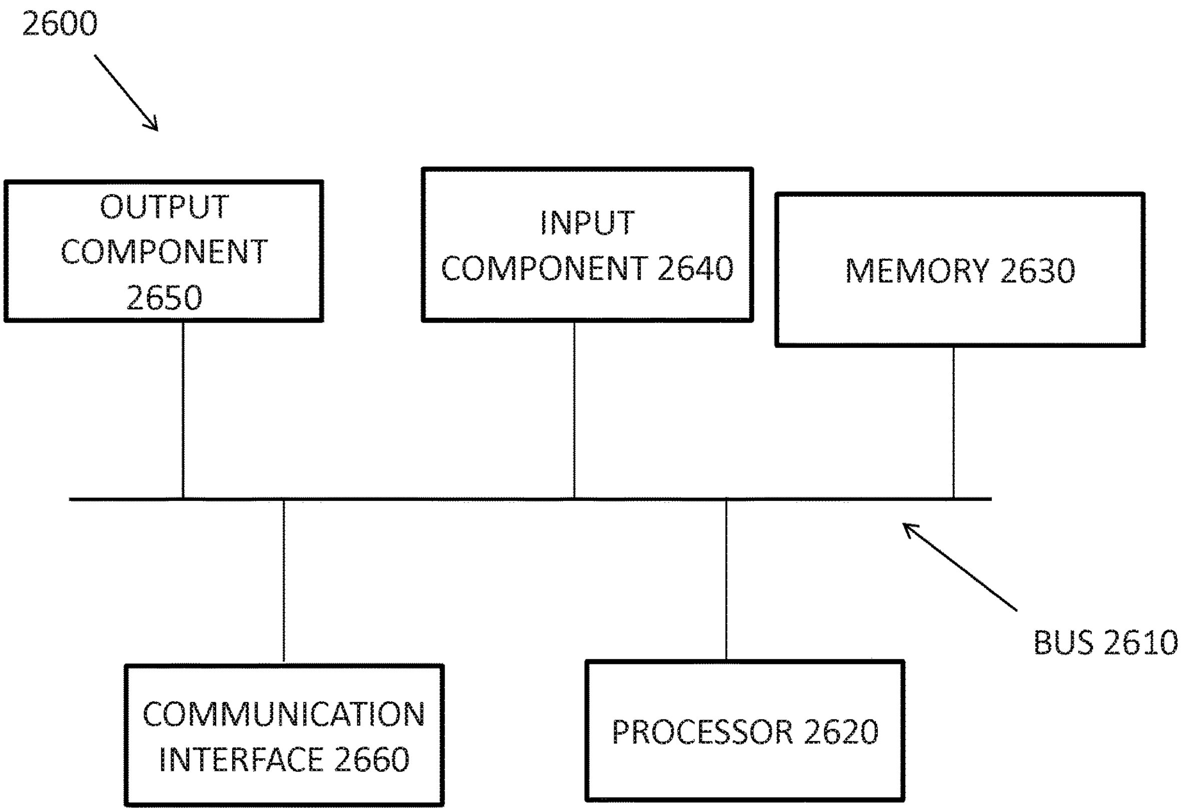
FIG. 26 is a diagram of an example computer.

FIG. 26 is a diagram of example components of a device 2600. Device 2600 may correspond to device 2502 and analysis system 2506. Alternatively, or additionally, device 2502 and analysis system 2506 may include one or more devices 2600 and/or one or more components of device 2600.

As shown in FIG. 26, device 2600 may include a bus 2610, a processor 2620, a memory 2630, an input component 2640, an output component 2650, and a communications interface 2660. In other implementations, device 2600 may contain fewer components, additional components, different components, or differently arranged components than depicted in FIG. 26. Additionally, or alternatively, one or more components of device 2600 may perform one or more tasks described as being performed by one or more other components of device 2600.

Bus 2610 may include a path that permits communications among the components of device 600. Processor 2620 may include one or more processors, microprocessors, or processing logic (e.g., a field programmable gate array (FPGA) or an application specific integrated circuit (ASIC)) that interprets and executes instructions. Memory 2630 may include any type of dynamic storage device that stores information and instructions, for execution by processor 2620, and/or any type of non-volatile storage device that stores information for use by processor 2620. Input component 2640 may include a mechanism that permits a user to input information to device 2600, such as a keyboard, a keypad, a button, a switch, voice command, etc. Output component 2650 may include a mechanism that outputs information to the user, such as a display, a speaker, one or more light emitting diodes (LEDs), etc.

Communications interface 2660 may include any transceiver-like mechanism that enables device 2600 to communicate with other devices and/or systems. For example, communications interface 2660 may include an Ethernet interface, an optical interface, a coaxial interface, a wireless interface, or the like.

In another implementation, communications interface 2660 may include, for example, a transmitter that may convert baseband signals from processor 2620 to radio frequency (RF) signals and/or a receiver that may convert RF signals to baseband signals. Alternatively, communications interface 2660 may include a transceiver to perform functions of both a transmitter and a receiver of wireless communications (e.g., radio frequency, infrared, visual optics, etc.), wired communications (e.g., conductive wire, twisted pair cable, coaxial cable, transmission line, fiber optic cable, waveguide, etc.), or a combination of wireless and wired communications.

Communications interface 2660 may connect to an antenna assembly (not shown in FIG. 26) for transmission and/or reception of the RF signals. The antenna assembly may include one or more antennas to transmit and/or receive RF signals over the air. The antenna assembly may, for example, receive RF signals from communications interface 2660 and transmit the RF signals over the air, and receive RF signals over the air and provide the RF signals to communications interface 660. In one implementation, for example, communications interface 2660 may communicate with network 2501.

As will be described in detail below, device 2600 may perform certain operations. Device 2600 may perform these operations in response to processor 2620 executing software instructions (e.g., computer program(s)) contained in a computer-readable medium, such as memory 2630, a secondary storage device (e.g., hard disk, CD-ROM, etc.), or other forms of RAM or ROM. A computer-readable medium may be defined as a non-transitory memory device. A memory device may include space within a single physical memory device or spread across multiple physical memory devices. The software instructions may be read into memory 2630 from another computer-readable medium or from another device. The software instructions contained in memory 2630 may cause processor 2620 to perform processes described herein. Alternatively, hardwired circuitry may be used in place of or in combination with software instructions to implement processes described herein. Thus, implementations described herein are not limited to any specific combination of hardware circuitry and software.

It will be apparent that example aspects, as described above, may be implemented in many different forms of software, firmware, and hardware in the implementations illustrated in the figures. The actual software code or specialized control hardware used to implement these aspects should not be construed as limiting. Thus, the operation and behavior of the aspects are described without reference to the specific software code—it being understood that software and control hardware could be designed to implement the aspects based on the description herein.

Even though particular combinations of features are recited in the claims and/or disclosed in the specification, these combinations are not intended to limit the disclosure of the possible implementations. In fact, many of these features may be combined in ways not specifically recited in the claims and/or disclosed in the specification. Although each dependent claim listed below may directly depend on only one other claim, the disclosure of the possible implementations includes each dependent claim in combination with every other claim in the claim set.

While various actions are described as selecting, displaying, transferring, sending, receiving, generating, notifying, and storing, it will be understood that these example actions are occurring within an electronic computing and/or electronic networking environment and may require one or more computing devices, as described in FIG. 25, to complete such actions. Also, any annotations or markings generated on an image (in the above figures) may be of any color, including white, black, or another color.

No element, act, or instruction used in the present application should be construed as critical or essential unless explicitly described as such. Also, as used herein, the article “a” is intended to include one or more items and may be used interchangeably with “one or more.” Where only one item is intended, the term “one” or similar language is used. Further, the phrase “based on” is intended to mean “based, at least in part, on” unless explicitly stated otherwise.

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. A method, comprising, receiving, by a computing device, two-dimensional images, wherein the two-dimensional images are slices from three-dimensional electronic scans, and wherein the two-dimensional images are for a region of interest within a person's mouth; and generating, by the computing device, a benchmark database;

wherein the benchmark database includes:

views of different mouth areas, wherein the different mouth areas have different image sizes, and wherein the different image sizes are all resized to a uniform rectangular dimension of 210×300;

previous information from dentists relating to annotations on the views of the different mouth areas, wherein the annotations are electronic line imagery placed over the mandibular canal area;

bilateral mandible electronic images, wherein the bilateral mandible electronic images is a full panoramic view of the mouth; and unilateral mandible electronic images;

applying, by the computing device, a mask over the images with the annotations on the views of the different mouth areas such that only the annotations are visible;

determining, by the computing device, a mandibular canal area within the person's mouth, wherein the determining the mandibular canal area within the person's mouth is based on the electronic line imagery placed over the mandibular and also includes segmenting the three-dimensional electronic scans into non-overlapping regions, wherein the non-overlapping regions include:

a foreground region that includes the mandibular canal area, wherein the foreground region has a first type of pixel, and a background region that includes other areas of the mouth but not the mandibular canal area, wherein the background region has a second type of pixel, wherein the segmenting further includes:

a segmentation model, denoted as $M_s$, which is trained using paired training data $$D = \{x_i, y_i\}_{i=1}^{N},$$

where $x_i$, represent the input image $y_i$ is a target (ground-truth) mask,

N is the total number of samples in D, where the input image is denoted as $x_i \in R^{n \times m \times 3}$, a target segmentation defined as $y_i \in \{0,1\}^{n \times m}$, which consists of an image containing pixels intensities of 1 and 0, wherein:

1 is the foreground (mandibular canal), 0 is the background, respectively, n is a first number of rows in input images, and m is a second number of rows in input images and masks.

2. The method of claim 1, wherein the received two-dimensional images is preprocessed data that has irrelevant electronic information removed.

3. The method of claim 1, wherein the different mouth areas include full head views, medium views, and small views.

4. The method of claim 1, wherein 80% of the benchmark database is used for training and 20% of the benchmark database is used for testing.

5. The method of claim 1, wherein the annotations are white in color.

* * * * *